United States Patent [19]

Callahan et al.

[11] 4,443,555
[45] Apr. 17, 1984

[54] METHOD FOR THE PREPARATION OF HIGH ACTIVITY PHOSPHOMOLYBDIC ACID BASED CATALYSTS

[75] Inventors: James L. Callahan, Wooster; Wilfrid G. Shaw; Arthur F. Miller, both of Lyndhurst, all of Ohio

[73] Assignee: The Standard Oil Company, Cleveland, Ohio

[21] Appl. No.: 439,704

[22] Filed: Nov. 8, 1982

Related U.S. Application Data

[62] Division of Ser. No. 271,487, Jun. 8, 1981, abandoned.

[51] Int. Cl.$^3$ .............................................. B01J 27/14
[52] U.S. Cl. ...................................... 502/211; 502/212
[58] Field of Search ................................. 502/211, 212

[56] References Cited

U.S. PATENT DOCUMENTS

| | | | |
|---|---|---|---|
| 3,238,254 | 3/1966 | Kerr | 260/530 |
| 3,642,930 | 2/1972 | Grasselli et al. | 260/680 E |
| 3,865,873 | 2/1975 | Oda et al. | 252/437 |
| 3,882,047 | 5/1975 | Niina et al. | 252/435 |
| 3,959,182 | 5/1976 | Izawa et al. | 252/467 |
| 3,975,300 | 8/1976 | Burress | 252/435 |
| 3,997,600 | 12/1976 | Ferlazzo et al. | 260/530 N |
| 4,000,088 | 12/1976 | Shimizu et al. | 252/437 |
| 4,003,978 | 1/1977 | Shiraishi et al. | 252/437 |
| 4,035,417 | 7/1977 | Izawa et al. | 252/435 |
| 4,077,912 | 3/1978 | Dolhyj et al. | 252/461 |
| 4,083,805 | 4/1978 | White et al. | 252/437 |
| 4,136,110 | 1/1979 | White et al. | 252/437 |
| 4,138,366 | 2/1979 | Shaw et al. | 252/464 |
| 4,147,661 | 4/1979 | Higgins et al. | 252/435 |
| 4,158,671 | 6/1979 | Barone | 252/437 X |
| 4,192,951 | 3/1980 | Slinkard et al. | 562/549 |
| 4,283,307 | 8/1981 | Barone et al. | 252/437 X |
| 4,360,453 | 11/1982 | Lemanski et al. | 252/437 X |

FOREIGN PATENT DOCUMENTS

| | | | |
|---|---|---|---|
| 47-33082 | 8/1972 | Japan . | |
| 1523849 | 9/1978 | United Kingdom | 562/599 |

*Primary Examiner*—William G. Wright
*Attorney, Agent, or Firm*—Joseph G. Curatolo; Larry W. Evans

[57] ABSTRACT

The present invention relates to a method for the preparation of phosphomolybdic acid based catalysts by forming a solution of hydrated phosphomolybdic acid in a substantially anhydrous alkyl alcohol, heating the solution to form a concentrate, and thereafter drying and calcining the concentrate support material so as to form the catalyst. Because the catalyst is prepared in alcoholic rather than aqueous solution, it has a greater activity in converting aldehydes to their respective unsaturated carboxylic acids than known phosphomolybdic acid based catalysts. Furthermore, the deammoniation step of the prior art is no longer required.

21 Claims, No Drawings

METHOD FOR THE PREPARATION OF HIGH ACTIVITY PHOSPHOMOLYBDIC ACID BASED CATALYSTS

This is a division of application Ser. No. 271,487 filed June 8, 1981, now abandoned. cl TECHNICAL FIELD Catalysts comprising phosphomolybdic acid and various salts thereof have recognized utility in several areas of petrochemical processing. An area of particular importance which relates to the present invention is the use of phosphomolybdic acid based compounds as catalysts for the selective direct oxidation of aldehydes such as isobutyraldehyde and methacrolein to their corresponding carboxylic acid, methacrylic acid. Catalysis with supported or unsupported dehydrated phosphomolybdic acid in combination with small amounts of promoters such as antimony, arsenic, bismuth, copper, tellurium and hydroxides or decomposable salts of alkali and alkaline earth metals is a process of specific economic interest. The subject invention sets forth a method for the preparation of phosphomolybdic acid based catalysts having a high activity for the more efficient conversion of aldehydes to unsaturated carboxylic acids.

BACKGROUND ART

Catalysts for the oxidation of unsaturated aldehydes to unsaturated acids are generally well known in the literature and in various patents. U.S. Pat. Nos. 2,865,873 and 3,882,047 and Japanese Pat. No. 47-33082 disclose such catalysts wherein ammonia or an ammonium-containing compound is incorporated in the preparation of the catalysts.

U.S. Pat. No. 2,865,873 in Column 13, Examples 101 to 104 discloses a process for the preparation of methacrylic acid using catalysts consisting of molybdenum, phosphorus, titanium and oxygen, wherein ammonium para-molybdate is employed in the preparation of the catalysts. The highest yield of methacrylic acid produced is about 39.56%.

U.S. Pat. No. 3,882,047 discloses the preparation of methacrylic acid using catalysts containing molybdenum, phosphorus, at least one element such as thallium, rubidium, cesium and potassium, and at least one element such as chromium, silicon, aluminum, iron and titanium. This reference teaches the incorporation of ammonia or ammonium-containing compounds in the preparation of catalysts exemplified in the oxidation of methacrolein or acrolein; phosphomolybdic acid is employed in the preparation of virtually all catalysts exemplified; and in a few examples, ammonium molybdate is employed. This patent discloses in Column 3, lines 30–40 as follows:

"It is preferred that the catalyst be prepared so that the constituent elements will form complex compounds such as heteropolyacids, then acid salts or ammonium salts."

Japanese Pat. No. 47-33082 discloses a process for reclaiming an ammonia-modified phosphorous-molybdenum-X-oxygen catalyst, wherein X is at least one element selected from the group consisting of antimony, arsenic, bismuth, cadmium, germanium, indium, iron, lead, silicon, thallium, tin and tungsten. Preparation of the catalyst involves treating the catalyst with the ammonia and water by oxidizing the catalyst in advance or by oxidizing it simultaneously with the treatment of ammonia and water. This patent discloses that the ammonia forms a complex compound with the other elements present.

Preparation of phosphomolybdic acid based catalyst in the absence of ammonia or ammonia-containing compound is described in U.S. Pat. No. 4,136,110, commonly owned by the Assignee of record herein. However, the process set forth therein is also directed toward catalysts preparation from molybdenum trioxide. Thus, the prior art of which we are aware has not set forth a method by which a phosphomolybic acid based catalyst can be prepared in aqueous media from phosphomolybic acid in the absence of ammonia or other basic compound.

Copending application Ser. No. 228,821 by Grasselli et al., assigned by our common Assignee herein, is directed to the preparation of first stage oxide catalysts containing molybdenum and one of bismuth or tellurium in an organic liquid preferably admixed with 5 to 35% water.

U.S. Pat. Nos. 3,959,182 and 4,035,417 disclose the preparation of molybdenum vanadate catalysts having a molybdenum oxide to vanadium oxide weight ratio of 2:1 to 8:1 in an aqueous solution to which is added various organic reducing agents. The liquid media exemplified contain between 4 to 8% organics by weight.

DISCLOSURE OF THE INVENTION

It is therefore an object of the present invention to provide a method for the preparation of phosphomolybic acid based catalysts having enhanced activity for the oxidation of aldehydes to unsaturated carboxylic acids.

It is a further object of the present invention to provide a method for the preparation of phosphomolybdic acid based catalysts utilizing phosphomolybdic acid without the presence of ammonia or other ammonia-containing compounds.

It is a further object of the present invention to provide a method for the preparation of phosphomolybdic acid based catalysts in an alcoholic catalyst solution which avoids gross precipitation of solids.

It is a further object of the present invention to provide a method for the preparation of phosphomolybdic acid based catalysts in an alcoholic catalyst solution which permits the impregnation of porous preformed supports.

These and other objects, together with the advantages thereof over known methods, which shall become apparent from the specification which follows, are accomplished by the invention as hereinafter described and claimed.

In general, the method of the present invention involves the steps of forming a solution of hydrated phosphomolybdic acid in a substantially anhydrous alcohol, heating the solution to form a dried catalyst precursor, and calcining the catalyst precursor. In the alternative, the solution can be heated to form a concentrate or a dried precursor powder, and a catalyst support is coated with the concentrate or with the precursor powder (e.g., by method set forth in U.S. Pat. No. 4,077,912). Thereafter, the coated catalyst is formed by calcining. Suitable promoter-containing compounds may optionally be added during the step of forming a solution. Alternatively, the alcoholic phosphomolybdic acid solution, with or without the additional components described hereinabove, may be employed to impregnate a porous preformed support material. Drying the impregnated support to remove the alcoholic solvent, followed by calcining, completes this alternate catalyst preparation procedure.

PREFERRED MODE FOR CARRYING OUT THE INVENTION

The inventive catalyst preparation technique is applicable to phosphomolybic acid based catalysts which are known in the art as second stage catalysts. This is in contrast to the method disclosed in U.S. Ser. No. 222,821 to Grasselli et al., assigned to our common Assignee and directed to the preparation of bismuth molybdate first stage catalysts in a precatalyst slurry in an organic liquid or a mixture of an organic liquid and water. By "first stage" catalysts is meant that the catalysts show good activity in the conversion of olefins to aldehydes such as propylene to acrolein but poor activity in the conversion of aldehydes to acids such as acrolein to acrylic acid. First stage catalysts are distinguished from "second stage" catalysts, which are catalysts showing poor activity in the conversion of propylene to acrolein but good activity in the conversion of acrolein to acrylic acid, and still other oxidation catalysts which are neither first stage catalysts nor second stage catalysts, e.g. maleic anhydride catalysts.

Because of the complexity of oxide complex oxidation catalysts, there is no clear understanding in the art of exactly what features of a catalyst (e.g. composition, crystal structure, calcination history, etc.) make it function as a first stage, second stage or different type of catalyst. Certain observations, however, can be made. For example, second stage catalysts cannot normally be calcined for any length of time at temperatures above about 1,000° F. (537° C.), since they lose most if not all of their activity if treated in this way. On the other hand, first stage catalysts work best if calcined (final calcination) above 1,000° F., such as for example at 610° C. In addition, it appears that first stage catalysts are "neutral" in character while second stage catalysts are "acidic" in character.

Empirically it is possible to make a rough approximation of the acidic or basic character of an oxide complex by comparing the total positive valences of the cationic elements with the total negative valences of the metalate moieties derived from the anionic acting elements. Because some cationic elements such as iron may exist in more than one valence state and because of the amphoteric elements, this approximation cannot be too exact. In any event, using this type analysis it appears that most second stage catalysts have a significant excess of anionic species, i.e. are highly acidic, while most first stage catalysts have a reasonable balance of cationic and anionic ingredients and hence are relatively neutral. Analytically, however, it is extremely difficult or impossible to determine if such oxide complexes, which are oxides and not acids or bases, exhibit an acidic or basic character. For this reason, the "neutral"/"acid" designations for first and second stage catalysts are still regarded as unconfirmed speculation. However, it is known that first and second stage catalysts are materially different from one another and from catalysts exhibiting neither first stage activity or second stage activity and that these differences can easily be determined by testing the catalyst in the first and second stage reactions as described above.

The catalyst commonly employed in the preparation of methacrylic acid from methacrolein or isobutyraldehyde and acrylic acid from acrolein is a phosphomolybdic acid based catalyst which can be provided with one or more metallic promoters and which has the general formula $Mo_xP_yA_aB_bC_cD_dE_eO_z$. Suitable promoters include the following: wherein A is, cesium, potassium, rubidium and/or thallium; B is copper and/or vanadium; C is antimony, arsenic, bismuth and/or tellurium; D is palladium; E is aluminum, barium, calcium, cerium, chromium, cobalt, iron, magnesium, manganese, nickel, tantalum, titanium, tungsten, zinc, zirconium, chlorine and/or bromine; and, wherein x can be 6 to 14 and is preferably 9 to 12, y can be 0.1 to 15 and is preferably 1 to 1.5, a can be 0.1 to 3 and is preferably 1 to 2, b can be 0.1 to 3 and is preferably 0.1 to 1, c can be 0 to 2 and is preferably 0 to 0.7, d can be 0 to 2 and is preferably 0 to 1, e can be 0 to 4 and is preferably 0 to 1, and z is a number necessary to satisfy the other elements. Suitable catalysts and the preparation thereof have been described in several U.S. patents commonly owned by the Assignee of record herein and include, for instance, U.S. Pat. Nos. 4,083,805 and 4,138,366. Of these many catalysts, those having a ratio of molybdenum to phosphorus or from about 3:1 to as high as 15:1 can be employed with 9 to 12:1 being preferred. Addition of these promoters can be made by employing the acids or decomposable salts of the promoters.

Inasmuch of these catalysts are known, the specific composition is not critical to the practice of the method set forth herein. Thus, while a particular formulation is employed in this disclosure by way of exemplification, it is to be understood that phosphomolybdic acid based compositions having other promoters could also be prepared according to the present invention.

Preparation of the catalyst involves as a first step the dissolving of hydrated phosphomolybdic acid in a substantially anhydrous alkyl alcohol. The preferred alcohol employed is ethanol although other lower alkyl alcohols having one to about five carbon atoms can be substituted therefor. Representative alcohols include but are not limited to methanol, ethanol, isopropanol, isobutanol and the like. The catalyst promoters can be added in some instances as acids or as salts. The one or more that is selected is also preferably dissolved in the substantially anhydrous alcohol so that the alcohol solution comprises a mixture of hydrated phosphomolybdic acid and the promoter-containing compounds.

It is necessary that the alcohol is substantially anhydrous. The presence of significant amounts of water in the solution diminishes the enhancement of catalyst processing and activity achieved by utilization of the alcohol solution.

The next step of the process involves heating the solution to form a concentrate. This is conducted at about the boiling point of the alcohol with stirring until either the volume has been reduced sufficiently for the catalyst mixture to fill the pore volume and wet-out the surface of a preformed fluid catalyst support or until the point of solidification is reached. In the latter instance, the solidified residue or catalyst precursor may be tabletted, pelleted, or may be moistened with alcohol and used to impregnate or coat a catalyst support. Suitable support materials include silica, alumina, alumina-silica, silicon carbide, niobium oxide, boron-phosphate, titania, zirconia and the like and preferably Alundum as well as mixtures thereof. Irrespective of the point at which the support is impregnated or coated with the concentrate, original solution or as the redissolved or powdered residue, the amount of active ingredient in the finished supported catalyst is generally from about 10 to 100 percent by weight and preferably up to about 70 percent. Additionally, inert diluents known in the art may be incorporated into the pelleted, tabletted or supported catalyst.

The formed catalyst is finally given a step of heating first to evaporate any remnant alcohol then subsequently to dry and calcine the catalyst. Evaporation is conducted at approximately the boiling point of the alcohol, drying at about 150° C. and calcining above 300° C. As will be recognized by those skilled in the art, temperatures high enough to degrade the catalyst should be avoided.

In the example which follows, a phosphomolybdic acid based catalyst having the composition $Mo_{10}PAs_{0.2}Cu_{0.2}O_z$ was prepared and coated on Alundum having a particle size between 10 and 20 mesh. Weight percent of active catalyst was 28.6. The catalyst thus prepared was thereafter tested for methacrolein oxidation at 375° C. In order to evaluate the effectiveness of the method set forth herein, a measurement of percent per single pass yield or percent yield was made, which is defined as follows:

$$\text{Percent Single Pass Yield} = \frac{\text{Moles of product recovered}^{(5493)}}{\text{Moles of reactant fed}} \times 100$$

EXAMPLE 1.2510 gm of $20\ MoO_3.2H_3PO_4.48H_2O$ was dissolved in 15 cc of substantially anhydrous ethanol with heating and stirring. Two additional solutions were made by dissolving 0.0202 gm of $H_3AsO_4.0.5H_2O$ and 0.0254 gm of $Cu(C_2H_3O_2)_2.H_2O$ in 5 cc of substantially anhydrous ethanol each. Both of these solutions were then added to the phosphomolybdic acid solution and the resulting mixture was heated with stirring at moderate heat until it just solidified. The residue that formed was redissolved in several drops of substantially anhydrous alcohol and impregnated on 2.5 gm 10–20 mesh Alundum particles in a jar followed by alternate heating and rotation of the jar to evaporate the alcohol. The impregnated catalyst was thereafter dried for 30 minutes at 150° C. and then calcined for 2 hours at 320° C. The calcined particles were again screened to insure a 10–20 mesh size fraction.

The resulting second stage catalyst was thereafter utilized with a conventional first stage catalyst to oxidize isobutylene to methacrolein and then methacrylic acid as follows: 2 cc of the second stage phosphomolybdic acid based catalyst was placed over 4 cc of the first stage oxidation catalyst. Testing was conducted in a flow microreactor consisting of a 0.79 cm I.D.×16.51 cm long stainless steel tube immersed in a molten salt bath at 375° C. and atmospheric pressure. Reactant feed comprising air, water and isobutylene, molar ratio of 12:3:1, was introduced into the bottom of the reactor through a 0.48 cm O.D. stainless steel preheat leg; the reactor and preheat leg forming a U-tube configuration. Within the reactor was a suitable first stage catalyst for the conversion of isobutylene to methacrolein on top of which was stacked the candidate second stage catalyst for the conversion of methacrolein to methacrylic acid. Process water was fed through a silicone rubber septum at the top of the preheat leg with a model 355 Sage syringe pump being used to regulate the process water flow rate. First stage conversion, i.e., isobutylene to methacrolein, was conducted by feeding isobutylene, air and water through the microreactor for an apparent contact time with 4 cc of the first stage catalyst of two seconds. The particular first stage catalyst employed was 20% silica and 80% active ingredients, the latter comprising a nickel-cobalt promoted bismuth molybdate catalyst as disclosed in U.S. Pat. No. 3,642,930. Results of the first stage oxidation were 98% total conversion with 76% yield of methacrolein, 11% methacrylic acid and the remainder being oxides of carbon. For the second stage conversion, methacrolein to methacrylic acid, an apparent contact time of one second was provided. The second stage catalyst was at the 28.6 weight percent level, supported on 10–20 mesh Alundum particles. Percent yields after the second stage oxidation were as follows:

Methacrolein: 21.9;
Methacrylic Acid: 56.0.

From an analysis of the products it was determined that isobutylene conversion was 100 percent. The formula for isobutylene conversion is as follows:

$$\frac{\text{Moles of isobutylene reacted}}{\text{Moles of isobutylene fed}} \times 100$$

Thus, it can be seen that the method set forth herein is effective in the preparation of second stage, phosphomolybdic acid based catalysts. Unlike conventional activation methods, which employ aqueous solutions of phosphomolybdic acid with or without promoters, the use of an alcoholic solution does not necessitate treatment with ammonia or similar basic compound. It is believed that the utility of the lower alcohols in this regard depends on thier solvency for phosphomolybdic acid and other catalyst constituents and on their ability to undergo chemical reaction with and solubilize the phosphomolybdic acid.

Another important aspect of this method of catalyst preparation is in the fact that by utilizing an alcoholic catalyst solution, the properties of a true solution are maintained, that is, there is no gross precipitation of solids, even in highly concentrated solution. By contrast, when ammonium ion must be introduced, as in the conventional preparations from aqueous solution, there is gross precipitation of insoluble ammonium phosphomolybdate. Another important consequence of the solution property of the phosphomolybdic acid alcohol system is that it permits the impregnation of porous preformed supports. This opportunity is not present where a large amount of the catalyst components exist as suspended solids within the impregnating fluid. The ability to impregnate a preformed porous support to produce an active and attrition resistant catalyst particle is particularly important in fluid-bed catalytic processing applications.

A further advantage of the phosphomolybdic acid-alcohol system resides in the protection of particular chemical groupings in the final drying and early calcination stages of catalyst preparation. This superiority of the alcohol is reflected in the high level of activity of the finished phosphomolybdic acid based catalyst.

The present invention provides a process for the production of unsaturated carboxylic acids from their corresponding aldehydes, saturated or unsaturated, in the presence of a phosphomolybdic acid based catalyst prepared as described above. The aldehyde is contacted with molecular oxygen in the vapor phase at a reaction temperature of about 200° C. to about 500° C. in the presence of the catalyst. Reaction pressure may be subatmospheric, atmospheric, or superatmospheric. The reaction may be conducted in fixed or fluid bed reactors.

Based upon the satisfactory yields of methacrylic acid that have been obtained when a second stage, phosphomolybdic acid based catalyst has been prepared according to the method set forth herein, it should be apparent that the objects of the invention have been met. It is to be understood that the preparation disclosed herein is applicable in general to phosphomolybdic acid based catalysts which, as stated hereinabove, can include one or more promoters or promoter-containing compounds. Presence or absence of these additional elements or compounds will not effect the method of preparation set forth herein.

It should also be apparent to those skilled in the art that the subject invention is operable on phosphomolybdic acid based catalysts having certain ratios of molybdenum to phosphorous and it is operable when certain alcohols, temperatures and catalyst supports are employed. It is to be understood that these variables fall within the scope of the claimed invention and that the subject invention is not to be limited by the example set forth herein. It has been provided merely to provide a demonstration of operability and it is believed that the selection of specific alcohols and reaction conditions can be determined without departing from the spirit of the invention herein disclosed and described, and that the scope of the invention shall include all modifications and variations that fall within the scope of the attached claims.

We claim:

1. A method for the preparation of second stage phosphomolybdic acid based catalysts comprising the steps of:
    forming a solution of hydrated phosphomolybdic acid in a substantially anhydrous alkyl alcohol;
    heating said solution to form a concentrate; and
    drying and calcining said concentrate so as to form the catalyst.

2. A method for the preparation of phosphomolybdic acid based catalysts, as set forth in claim 1, including the additional step of treating a catalyst support material with said concentrate, and thereafter drying and calcining said concentrate and said support material treated therewith.

3. A method for the preparation of phosphomolybdic acid based catalysts, as set forth in claim 1, including the additional step of adding at least one promoter-containing compound selected from the group consisting of acids and decomposable salts of promoters selected from the group consisting of, cesium, potassium, rubidium, thallium, copper, vanadium, antimony, arsenic, bismuth, tellurium, palladium, aluminum, barium, calcium, cerium, chromium, cobalt, iron, magnesium, manganese, nickel, tantalum, titanium, tungsten, zinc, zirconium, chlorine and bromine.

4. A method for the preparation of phosphomolybdic acid based catalysts, as set forth in claim 1, wherein the step of heating is conducted until a solidified residue is formed.

5. A method for the preparation of phosphomolybdic acid based catalysts, as set forth in claim 4, including the further steps of moistening said residue with a substantially anhydrous alcohol and thereafter treating a catalyst support material therewith.

6. A method for the preparation of phosphomolybdic acid based catalysts, as set forth in claim 1, wherein the step of heating is conducted until the volume has been reduced sufficiently for the catalyst mixture to fill the pore volume and wet-out the surface of a catalyst support material.

7. A method for the preparation of phosphomolybdic acid based catalysts, as set forth in claim 2 wherein said catalyst support material is selected from the group consisting of alumina, Alundum, boron-phosphate, silica, alumina-silica, silicon carbide, niobium oxide, titania, and zirconia and mixtures thereof.

8. A method for the preparation of phosphomolybdic acid based catalysts, as set forth in claim 1 wherein said anhydrous alkyl alcohol has from one to about five carbon atoms.

9. A method for the preparation of phosphomolybdic acid based catalysts, as set forth in claim 8, wherein said anhydrous alkyl alcohol is ethanol.

10. A method for the preparation of phosphomolybdic acid based catalysts, as set forth in claim 1, wherein the step of drying is conducted at a temperature of at least 150° C. and the step of calcining is conducted at a temperature of at least 300° C.

11. A method for the preparation of phosphomolybdic acid based catalysts, as set forth in claim 3, wherein said phosphomolybdic acid based catalyst has the formula $Mo_xP_yA_aB_bC_cD_dE_eO_z$, wherein A is selected from the group consisting of, cesium, potassium, rubidium and thallium; B is selected from the group consisting of copper and vanadium; C is selected from the group consisting of antimony, arsenic, bismuth and tellurium; D is palladium; E is aluminum, barium, calcium, cerium, chromium, cobalt, iron, magnesium, manganese, nickel, tantalum, titanium, tungsten, zinc, zirconium, chlorine and bromine; x is 6 to 14; y is 0.1 to 15; a is 0.1 to 3; b is 0.1 to 3; c is 0 to 2; d is 0 to 2; e is 0 to 4 and z is a number necessary to satisfy the other elements.

12. A method for the preparation of phosphomolybdic acid based catalysts, as set forth in claim 11, wherein x is 9 to 12; y is 1 to 1.5; a is 1 to 2; b is 0.1 to 1; c is 0 to 0.7; d is 0 to 1 and e is 0 to 1.

13. A method for the preparation of phosphomolybdic acid based catalysts, as set forth in claim 12, wherein the composition of said phosphomolybdic acid based catalyst is $Mo_{10}PAs_{0.2}Cu_{0.2}O_z$.

14. A method for the preparation of phosphomolybdic acid based catalysts, as set forth in claim 5 wherein said catalyst support material is selected from the group consisting of alumina, Alundum, boron-phosphate, silica, alumina-silica, silicon carbided, niobium oxide, titania, and zirconia and mixtures thereof.

15. A method for the preparation of phosphomolybdic acid based catalysts, as set forth in claim 6 wherein said catalyst support material is selected from the group consisting of alumina, Alundum, boron-phosphate, silica, alumina-silica, silicon carbide, niobium oxide, titania, and zirconia and mixtures thereof.

16. A method for the preparation of phosphomolybdic acid based catalysts, as set forth in claim 2 wherein said anhydrous alkyl alcohol has from one to about five carbon atoms.

17. A method for the preparation of phosphomolybdic acid based catalysts, as set forth in claim 3, wherein said anhydrous alkyl alcohol has from one to about five carbon atoms.

18. A method for the preparation of phosphomolybdic acid based catalysts, as set forth in claim 5 wherein said anhydrous alkyl alcohol has from one to five carbon atoms.

19. A method for the preparation of phosphomolybdic acid based catalysts, as set forth in claim 16, wherein said anhydrous alkyl alcohol is ethanol.

20. A method for the preparation of phosphomolybdic acid based catalysts, as set forth in claim 17, wherein said anhydrous alkyl alcohol is ethanol.

21. A method for the preparation of phosphomolybdic acid based catalysts, as set forth in claim 18, wherein said anhydrous alkyl alcohol is ethanol.

* * * * *